(12) United States Patent
Naylor et al.

(10) Patent No.: US 12,127,955 B2
(45) Date of Patent: Oct. 29, 2024

(54) TRIAL COMPONENT AND METHOD

(71) Applicant: DEPUY IRELAND UNLIMITED COMPANY, County Cork (IE)

(72) Inventors: Jason Naylor, Leeds (GB); Stephanie Prince, Wakefield (GB); Timothy Board, Lancashire (GB); John Bohannon Mason, Charlotte, NC (US); Ahmad Jalandari, Leeds (GB); Neil Woollen, Bradford (GB); Elsie Kirby, Leeds (GB)

(73) Assignee: DEPUY IRELAND UNLIMITED COMPANY, Co Cork (IE)

( * ) Notice: Subject to any disclaimer, the term of this patent is extended or adjusted under 35 U.S.C. 154(b) by 715 days.

(21) Appl. No.: 17/302,298

(22) Filed: Apr. 29, 2021

(65) Prior Publication Data
US 2022/0346976 A1 Nov. 3, 2022

(51) Int. Cl.
*A61F 2/46* (2006.01)
*A61F 2/36* (2006.01)
*A61B 17/16* (2006.01)

(52) U.S. Cl.
CPC .......... *A61F 2/4684* (2013.01); *A61F 2/3609* (2013.01); *A61F 2/3662* (2013.01); *A61B 17/1668* (2013.01); *A61F 2002/3625* (2013.01)

(58) Field of Classification Search
CPC .... A61F 2/4684; A61F 2/3609; A61F 2/3662; A61F 2002/3626; A61F 2002/30616;
(Continued)

(56) References Cited

U.S. PATENT DOCUMENTS

| 3,810,312 A | 5/1974 | Carson |
| 3,889,558 A | 6/1975 | Duncan |

(Continued)

FOREIGN PATENT DOCUMENTS

| CN | 1193899 A | 9/1998 |
| CN | 102048599 A | 5/2011 |

(Continued)

OTHER PUBLICATIONS

"Engage Modular Revision Hip System: Surgical Technique," 2007, DePuy Orthopaedics, Inc, 19 pages.
(Continued)

*Primary Examiner* — Alvin J Stewart

(57) ABSTRACT

A trial neck for hip surgery and a method of attaching a trial neck to a bone canal preparation instrument. The trial neck includes a body portion having a bore for receiving a proximal end of the bone canal preparation instrument. The trial neck also includes an elongate neck part comprising a pair of arms extending from the body portion. The trial neck further includes a clamping mechanism comprising a live spring formed by the body portion and said pair of arms of the elongate neck part and an actuator, for moving the clamping mechanism between a clamping configuration and a non-clamping configuration. In the clamping configuration, the pair of arms of the elongate neck part are pinched together to cause an inner wall of the bore to urge against the bone canal preparation instrument to retain the proximal end of the bone canal preparation instrument within the bore.

30 Claims, 12 Drawing Sheets

(58) Field of Classification Search
CPC .. A61F 2002/30614; A61F 2002/30607; A61F 2002/30329; A61F 2002/3652
See application file for complete search history.

(56) References Cited

U.S. PATENT DOCUMENTS

| | | | |
|---|---|---|---|
| 3,987,499 | A | 10/1976 | Scharbach |
| 4,305,394 | A | 12/1981 | Bertuch, Jr. |
| 4,601,289 | A | 7/1986 | Chiarizzio |
| 4,693,724 | A | 9/1987 | Rhenter |
| 4,959,066 | A | 9/1990 | Dunn |
| 4,962,155 | A | 10/1990 | Fujita Yamaguchi |
| 5,002,578 | A | 3/1991 | Luman |
| 5,002,581 | A | 3/1991 | Paxson |
| 5,041,118 | A | 8/1991 | Wasilewski |
| 5,057,112 | A | 10/1991 | Sherman |
| 5,190,550 | A | 3/1993 | Miller |
| 5,342,363 | A | 8/1994 | Richelsoph |
| 5,352,231 | A | 10/1994 | Brumfield |
| 5,409,492 | A | 4/1995 | Jones |
| 5,480,451 | A | 1/1996 | Grundei |
| 5,540,687 | A | 7/1996 | Fairley |
| 5,569,263 | A | 10/1996 | Hein |
| 5,653,764 | A | 8/1997 | Murphy |
| 5,653,765 | A | 8/1997 | McTighe |
| 5,766,261 | A | 6/1998 | Neal |
| 5,858,020 | A | 1/1999 | Johnson |
| 5,876,459 | A | 3/1999 | Powell |
| 5,888,208 | A | 3/1999 | Ro |
| 5,906,644 | A | 5/1999 | Powell |
| 5,938,701 | A | 8/1999 | Hiernard |
| 6,042,611 | A | 3/2000 | Noiles |
| 6,048,365 | A | 4/2000 | Burrows |
| 6,080,162 | A | 6/2000 | Dye |
| 6,090,146 | A | 7/2000 | Rozow, III |
| 6,110,179 | A | 8/2000 | Flivik |
| 6,149,687 | A | 11/2000 | Gray, Jr. |
| 6,165,177 | A | 12/2000 | Wilson |
| 6,193,759 | B1 | 2/2001 | Ro |
| 6,238,435 | B1 | 5/2001 | Meulink |
| 6,258,097 | B1 | 7/2001 | Cook |
| 6,330,845 | B1 | 12/2001 | Meulink |
| 6,447,518 | B1 | 9/2002 | Krause |
| 6,464,728 | B1 | 10/2002 | Murray |
| 6,491,696 | B1 | 12/2002 | Kunkel |
| 6,679,917 | B2 | 1/2004 | Ek |
| 6,702,854 | B1 | 3/2004 | Cheal |
| 6,706,072 | B2 | 3/2004 | Dwyer |
| 6,743,235 | B2 | 6/2004 | Subba Rao |
| 6,883,217 | B2 | 4/2005 | Barrette |
| 6,905,515 | B1 | 6/2005 | Gilbertson |
| 7,022,141 | B2 | 4/2006 | Dwyer |
| 7,066,042 | B2 | 6/2006 | Andrews |
| 7,135,044 | B2 | 11/2006 | Bassik |
| 7,188,556 | B1 | 3/2007 | Rinner |
| 7,297,166 | B2 | 11/2007 | Dwyer |
| 7,363,838 | B2 | 4/2008 | Abdelgany |
| 7,572,297 | B2 | 8/2009 | Cheal |
| 7,582,092 | B2 | 9/2009 | Jones |
| 7,585,329 | B2 | 9/2009 | McCleary |
| 7,601,155 | B2 | 10/2009 | Petersen |
| 7,641,698 | B1 | 1/2010 | Gibbs |
| 7,981,161 | B2 | 7/2011 | Choi |
| 8,048,167 | B2 | 11/2011 | Dietz |
| 8,449,619 | B2* | 5/2013 | Metcalfe ............... A61F 2/4684 623/22.11 |
| 11,344,437 | B2* | 5/2022 | Bailey ................ A61B 17/1659 |
| 2002/0038148 | A1 | 3/2002 | Fernandez |
| 2002/0058999 | A1 | 5/2002 | Dwyer |
| 2003/0074080 | A1 | 4/2003 | Murray |
| 2003/0149487 | A1 | 8/2003 | Doubler |
| 2004/0004186 | A1 | 1/2004 | Jiyan |
| 2004/0054373 | A1 | 3/2004 | Serra |
| 2004/0073315 | A1 | 4/2004 | Justin |
| 2004/0122437 | A1 | 6/2004 | Dwyer |
| 2004/0122439 | A1 | 6/2004 | Dwyer |
| 2004/0122440 | A1 | 6/2004 | Daniels |
| 2004/0122525 | A1 | 6/2004 | Daniels |
| 2004/0172139 | A1 | 9/2004 | Dwyer |
| 2004/0236341 | A1 | 11/2004 | Petersen |
| 2004/0267267 | A1 | 12/2004 | Daniels |
| 2004/0267372 | A1* | 12/2004 | Vanasse ............... A61F 2/4684 623/22.11 |
| 2004/0267373 | A1 | 12/2004 | Dwyer |
| 2005/0033444 | A1 | 2/2005 | Jones |
| 2005/0107799 | A1 | 5/2005 | Graf |
| 2005/0143828 | A1 | 6/2005 | Collins |
| 2005/0203634 | A1 | 9/2005 | Bassik |
| 2005/0245934 | A1 | 11/2005 | Tuke |
| 2006/0027027 | A1 | 2/2006 | Serra |
| 2006/0217737 | A1 | 9/2006 | Iversen |
| 2006/0241625 | A1* | 10/2006 | Metcalfe ............. A61B 17/162 606/79 |
| 2006/0260440 | A1 | 11/2006 | Abdelgany |
| 2007/0005144 | A1 | 1/2007 | Leisinger |
| 2007/0050039 | A1 | 3/2007 | Dietz |
| 2007/0100464 | A1 | 5/2007 | Meulink |
| 2007/0123908 | A1 | 5/2007 | Jones |
| 2007/0219641 | A1 | 9/2007 | Dorr |
| 2007/0233132 | A1 | 10/2007 | Valla |
| 2007/0244566 | A1 | 10/2007 | Daniels |
| 2008/0091212 | A1 | 4/2008 | Dwyer |
| 2008/0262626 | A1 | 10/2008 | Raugel |
| 2009/0048682 | A1 | 2/2009 | Choi |
| 2009/0112216 | A1 | 4/2009 | Leisinger |
| 2009/0112218 | A1 | 4/2009 | McCleary |
| 2009/0187251 | A1 | 7/2009 | Justin |
| 2009/0307887 | A1 | 12/2009 | Jones |
| 2010/0241239 | A1 | 9/2010 | Smith |
| 2010/0249943 | A1 | 9/2010 | Bergin |
| 2011/0054628 | A1 | 3/2011 | Banks |
| 2011/0302760 | A1 | 12/2011 | Leisinger |
| 2012/0053698 | A1 | 3/2012 | Huff |
| 2012/0259338 | A1 | 10/2012 | Carr |
| 2012/0259423 | A1 | 10/2012 | Carr |
| 2012/0259424 | A1* | 10/2012 | Hood ................... A61F 2/4684 623/23.35 |
| 2012/0290099 | A1 | 11/2012 | Gibson |
| 2013/0144397 | A1 | 6/2013 | Smith |
| 2013/0158674 | A1 | 6/2013 | Chow |
| 2013/0261762 | A1 | 10/2013 | Kennedy |
| 2014/0276866 | A1 | 9/2014 | Endsley |
| 2015/0018961 | A1* | 1/2015 | Huddle ................ A61F 2/4684 623/22.4 |
| 2015/0083116 | A1 | 3/2015 | Zhu |
| 2016/0030200 | A1 | 2/2016 | Hunt |
| 2016/0278945 | A1* | 9/2016 | Emerick .................. A61F 2/40 |
| 2019/0247063 | A1 | 8/2019 | Huff |
| 2020/0222208 | A1 | 7/2020 | Bushell |
| 2020/0276029 | A1* | 9/2020 | Bailey ................ A61B 17/1659 |
| 2020/0352742 | A1* | 11/2020 | Horne .................. A61F 2/4684 |
| 2021/0093332 | A1 | 4/2021 | Walker |
| 2022/0233337 | A1* | 7/2022 | Dmuschewsky ...... A61F 2/3601 |
| 2022/0241092 | A1* | 8/2022 | Board ................ A61B 17/1668 |
| 2022/0249256 | A1* | 8/2022 | Amaral ................ A61F 2/4607 |

FOREIGN PATENT DOCUMENTS

| | | |
|---|---|---|
| CN | 106264797 A | 1/2017 |
| DE | 20114835 U1 | 1/2002 |
| DE | 202007009646 U1 | 10/2007 |
| DE | 102007032014 B3 | 10/2008 |
| EP | 1000595 A1 | 5/2000 |
| EP | 1435223 A1 | 7/2004 |
| EP | 1522284 A2 | 4/2005 |
| EP | 1950396 A1 | 7/2008 |
| EP | 2055273 A1 | 5/2009 |
| EP | 2057969 A2 | 5/2009 |
| FR | 2574283 A1 | 6/1986 |
| FR | 2796267 A1 | 1/2001 |
| FR | 2832624 A1 | 5/2003 |
| FR | 2926212 A1 | 7/2009 |
| GB | 806441 A | 12/1958 |

(56) References Cited

FOREIGN PATENT DOCUMENTS

| | | | |
|---|---|---|---|
| GB | 2583537 | A | 4/2020 |
| JP | 5859810 | B2 | 2/2016 |
| WO | WO 1992003993 | A1 | 3/1992 |
| WO | WO 1996036284 | A1 | 11/1996 |
| WO | WO 1997030661 | A1 | 8/1997 |
| WO | WO 2002026145 | A1 | 4/2002 |
| WO | WO 2007098549 | A1 | 9/2007 |
| WO | WO 2008069800 | A1 | 6/2008 |
| WO | WO 2009106866 | A1 | 9/2009 |
| WO | WO 2009108683 | A1 | 9/2009 |
| WO | WO 20120352942 | A2 | 3/2012 |
| WO | WO 2012138824 | A2 | 10/2012 |
| WO | WO 2014140636 | A1 | 9/2014 |
| WO | WO 2014140639 | A1 | 9/2014 |
| WO | WO 2018189128 | A1 | 10/2018 |
| WO | WO 2019068428 | A1 | 4/2019 |

OTHER PUBLICATIONS

The Ranawat Sign A Specific Maneuver to Assess Component Positioning in Total Hip Arthroplasty, Lucas, David H., and Scott, Richard D., Journal of Orthopaedic Techniques, vol. 2, No. 2, Jun. 1994.

* cited by examiner

TRIAL COMPONENT AND METHOD

FIELD

The present specification relates to a trial component for orthopaedic surgery. In particular, a trial femoral neck for orthopaedic surgery. This disclosure also relates to a kit including one or more trial components, and instruments for orthopaedic surgery. This disclosure also relates to a method of performing orthopaedic surgery.

BACKGROUND

Hip replacement is a surgical procedure in which the hip joint is replaced by artificial joint components, also referred to generally as prostheses or implants. Total replacement of the hip joint involves installing an acetabular cup implant in the acetabulum of a patient and installing a prosthetic in the femur of the patient. Joint replacement surgery can also be performed in other joints, such as the shoulder.

For hip replacement surgery, the prosthetic typically includes a femoral stem, which is received in the medullary canal of the femur, and a femoral head having a bearing surface which is received in the acetabulum or acetabular cup implant. The prosthetic typically also includes a femoral neck which extends between a proximal end of the stem and the head.

Successful hip replacement surgery requires correct positioning and alignment of the acetabular cup implant as well as the prosthetic itself. Misalignment and/or the selection of an inappropriately sized acetabular cup implant and/or the prosthetic may result in restricted movement of the prosthetic and/or accelerated wear and tear of the bearing surfaces of the acetabular cup implant and the bearing surface of the head. Various factors are involved in achieving this correct positioning and alignment. At least some of these factors relate to the neck of the prosthetic. These factors may include, for instance, the length of the neck, and an angular orientation (offset) of the neck relative to the stem. Trialling may be used during such orthopaedic procedures in order to help assess the patient's needs.

Trialling can be used during primary or complex primary and revision surgeries. During trialling, the surgeon uses trial components, rather than the actual implants, to help assess whether any changes might be made to bone cuts and/or soft tissues and/or the implants originally planned to be used. It can be more efficient to utilise a bone canal preparation instrument as one of these components.

During a primary hip or shoulder arthroplasty procedure, various sizes of broach or other bone canal preparation instruments may be used to prepare the medullary canal of the femur or humerus. Once the bone canal preparation instrument is inserted into the bone, a trial neck and trial head may also be attached to the bone canal preparation instrument, in order to evaluate whether a prosthetic having a neck and head of that type (e.g. in terms of the size and offset of the neck) would be appropriate for the patient.

Conventionally trial necks are connected to the spigot of the bone canal preparation instrument by the use of an O-ring. The O-ring forms an interference fit or friction fit when it arranged between the spigot and the internal surface of the trial neck.

After the surgeon is satisfied that the chosen combination of bone canal preparation instrument, trial neck and trial head are correctly positioned and aligned, they may be removed and replaced with the implant itself.

Occasionally revision arthroplasty surgery may need to be performed on a patient. In such a revision surgery, the previously implanted prosthesis is surgically removed, and a replacement prosthesis is implanted. In some revision surgeries, all of the components of the previously implanted hip prosthesis, including, for example, the femoral stem, neck component, and the acetabular cup, may be surgically removed. In other revision surgeries, only part of the previously implanted prosthesis may be removed and replaced.

SUMMARY

Aspects of the present disclosure are set out in the accompanying independent and dependent claims. Combinations of features from the dependent claims may be combined with features of the independent claims as appropriate and not merely as explicitly set out in the claims.

According to a first aspect of this disclosure there is provided a trial neck for releasable attachment to a bone canal preparation instrument, the trial neck comprising:
  a body portion having a bore for receiving a proximal end of the bone canal preparation instrument;
  an elongate neck part comprising a pair of arms extending from the body portion;
  a clamping mechanism comprising a live spring formed by the body portion and said pair of arms of the elongate neck part; and
  an actuator, for moving the clamping mechanism between a clamping configuration and a non-clamping configuration,
  wherein in the clamping configuration, the pair of arms of the elongate neck part are pinched together to cause an inner wall of the bore to urge against the bone canal preparation instrument to retain the proximal end of the bone canal preparation instrument within the bore.

The pinching together of the pair of arms can narrow and/or distort the bore so that it can grip the proximal end of the bone canal preparation instrument to provide a secure attachment of the trial neck to the bone canal preparation instrument.

The clamping mechanism may allow the trial neck to be attached to a bone canal preparation instrument in a variety of orientations e.g. around a longitudinal axis of the bone canal preparation instrument.

The pair of arms may extend from the elongate neck part into the body portion, and the bore for receiving the proximal end of the bone canal preparation instrument may pass through the pair of arms.

The bore may be defined by a bore annulus and the pair of arms may be positioned such that an arm is located on either side of a break in the bore annulus. The break in the bore annulus promotes distortion of the bore when the pair of arms are pinched together.

The pair of arms may comprise a superiorly located arm and an inferiorly located arm.

The trial neck may further include a partially threaded actuator bore which extends through the pair of arms. The partially threaded actuator bore may be arranged such that one of the superior or inferior arm may comprise an unthreaded portion of the actuator bore, and the other of the superior or inferior arm comprises a threaded portion of the actuator bore. The actuator may comprise a threaded actuation member extending within the partially threaded actuator bore. The threaded actuator can provide a convenient way of operating the clamping mechanism. Further, the threaded actuator can allow fine adjustments to be made to the size of the bore for receiving the proximal end of the bone canal preparation instrument.

The actuator bore may extend substantially parallel to the bore for receiving the proximal end of the bone canal preparation instrument.

The elongate neck part may also comprise a proximal end; a distal end; and a neck axis extending between the proximal and distal ends. The actuator bore may extend from the proximal end to the distal end of the elongate neck part such that the actuator bore extends substantially parallel to a neck axis. This can allow the surgeon to have improved accessibility to the actuator bore when the actuator bore extends from the proximal end of the elongate neck part.

The elongate neck part may also comprise a proximal part, a distal part, and a neck axis extending between the proximal and distal parts. The distal part may comprise the pair of arms. The threaded actuator bore and threaded actuation member may be substantially parallel to the neck axis. The proximal part may be detachable from the distal part, wherein attachment of the proximal part onto the distal part causes the pair of arms of the elongate neck part to be pinched together to cause an inner wall of the bore to urge against the bone canal preparation instrument to retain the proximal end of the bone canal preparation instrument within the bore. This can allow the surgeon to have improved accessibility to the actuator bore when the actuator bore extends from the proximal end of the elongate neck part.

The actuator may comprise a trial head having a bore for connection to the trial neck, wherein attachment of the trial head over the proximal end of the elongate neck part causes the pair of arms of the elongate neck part to be pinched together to cause an inner wall of the bore to urge against the bone canal preparation instrument to retain the proximal end of the bone canal preparation instrument within the bore. This can reduce the number of parts needed to form the trial since there is no need for a separate actuation member.

The pair of arms may include a recess for engagement with a corresponding projection inside the bore of the trial head, wherein the recess has a variable depth along its length, and wherein rotation of the projection within the recess causes the pair of arms of the elongate neck part to be pinched together to cause an inner wall of the bore to urge against the bone canal preparation instrument to retain the proximal end of the bone canal preparation instrument within the bore. The recess allows the user to adjust the level of pinching by the arms, and so adjust the size of the bore for receiving the bone canal preparation instrument. This can reduce the number of parts needed to form the trial since there is no need for a separate actuation member. The rotation of projections within the recess is a convenient way of operating the clamping mechanism and using the trial head as the actuator can provide for an easily accessible mechanism for a surgeon.

The elongate neck part may comprise;
a proximal part and a distal part;
wherein the proximal part comprises a head attachment portion and an actuator bore;
wherein the distal part comprises the pair of arms, wherein the arms extend from the body portion, and wherein the bore for receiving the proximal end of the bone canal preparation instrument passes through the pair of arms,
wherein the proximal part of the elongate neck part is detachable from the distal part, and wherein attachment of the proximal part to the distal part causes the pair of arms to pinch together to cause an inner wall of the bore to urge against the bone canal preparation instrument to retain the proximal end of the bone canal preparation instrument within the bore.

This can provide increased leverage, because the arms are pinched together at the proximal end of the arms.

The pair of arms may be threaded at a proximal end of the distal part for connection to a corresponding thread on an inner wall of the actuator bore of the proximal part. This can provide for a secure connection between the distal and proximal parts.

The proximal end of the distal part may comprise at least one protrusion on an outer surface of the pair of arms. At least one protrusion may extend from an inner wall of the actuator bore. When assembled, a distal surface of the at least one protrusion on the proximal end of the distal part may abut a proximal surface of the at least one protrusion on the proximal part. Attachment of the proximal part to the distal part may cause the pair of arms to pinch together to cause an inner wall of the bore to urge against the bone canal preparation instrument to retain the proximal end of the bone canal preparation instrument within the bore. This mechanism can allow the user to quickly attach the proximal part to the distal part whilst activating the clamping mechanism.

The pair of arms may comprise an anteriorly located arm and a posteriorly located arm.

According to another aspect of this disclosure, there is provided a surgical kit comprising:
a trial neck according to any preceding claim; and
a bone canal preparation instrument.

The surgical kit may further comprise a trial head having a bore for receiving the proximal end of the elongate neck part to releasably attach the trial head to the trial neck. The surgical kit may further comprise a prosthetic stem component.

According to a further aspect of this disclosure, there is provided a method of attaching a trial neck to a bone canal preparation instrument, the trial neck comprising:
a body portion having a bore for receiving a proximal end of the bone canal preparation instrument;
an elongate neck part comprising a pair of arms extending from the body portion;
a clamping mechanism comprising a live spring formed by the body portion and said pair of arms of the elongate neck part; and
an actuator, for moving the clamping mechanism between a clamping configuration and a non-clamping configuration, the method comprising:
inserting the proximal end of the bone canal preparation instrument into the bore; and
using the actuator to pinch the pair of arms of the elongate neck part together to cause an inner wall of the bore to urge against the bone canal preparation instrument.

The pinching together of the pair of arms narrows the bore to provide a secure attachment of the trial neck onto the bone canal preparation instrument without the need for the bone canal preparation instrument to be at a specific angle or position. The trial neck can therefore be attached to a bone canal preparation instrument in a variety of orientations.

The pair of arms of the trial neck may extend from the elongate neck part into the body portion. The bore for receiving the proximal end of the bone canal preparation instrument may pass through the pair of arms.

The bore may be defined by a bore annulus and the pair of arms may be positioned such that an arm is located on either side of a break in the bore annulus. The break in the bore annulus promotes distortion of the bore when the pair of arms are pinched together. This allows retention of the proximal end of the reamer by both axial tension and torsional forces.

The break in the bore annulus may be transverse to the bore axis, or may be a longitudinal break, extending the length of the bore (parallel to the bore axis). A transverse break promotes distortion of the bore and provides axial tension against the proximal end of the reamer. A longitudinal break promotes distortion of the bore and provides torsional tension against the proximal end of the reamer. Both the transverse and longitudinal beaks provide a degree of axial tension and torsional forces.

The pair of arms may comprise a superiorly located arm and an inferiorly located arm.

A partially threaded actuator bore may extend through the pair of arms. The partially threaded actuator bore may be arranged such that one of the pair of arms may include a threaded portion of the actuator bore, while the other arm may include an un-threaded portion of the actuator bore. The actuator may comprise a threaded actuation member extending within the threaded actuator bore. The threaded actuator can provide a convenient way of operating the clamping mechanism. Further, the threaded actuator can allow fine adjustments to be made to the size of the bore for receiving the proximal end of the bone canal preparation instrument.

The actuator bore may extend substantially parallel to the bore for receiving the proximal end of the bone canal preparation instrument.

The elongate neck part may comprise:
a proximal end;
a distal end; and
a neck axis extending between the proximal and distal ends,
wherein the actuator bore extends from the proximal end to the distal end of the elongate neck part such that the actuator bore extends substantially parallel to a neck axis.

The elongate neck part may comprise:
a proximal part, a distal part, and a neck axis extending between the proximal and distal parts;
wherein the distal part comprises the pair of arms;
wherein the threaded actuator bore and threaded actuation member are substantially parallel to the neck axis; and
wherein the proximal part is detachable from the distal part, wherein attachment of the proximal part onto the distal part causes the pair of arms of the elongate neck part to be pinched together to cause an inner wall of the bore to urge against the bone canal preparation instrument to retain the proximal end of the bone canal preparation instrument within the bore.

The actuator may comprise a trial head having a bore for connection to the trial neck. The method may further comprise placing the trial head over the proximal end of the elongate neck part to pinch together the pair of arms of the elongate neck part, causing an inner wall of the bore to urge against the bone canal preparation instrument to retain the proximal end of the bone canal preparation instrument within the bore.

The pair of arms may include a recess for engagement with a corresponding projection inside the bore of the trial head. The recess may have a variable depth along its length. The method may further comprise rotating the trial head to rotate the projection within the recess to cause the pair of arms of the elongate neck part to pinch together to cause an inner wall of the bore to urge against the bone canal preparation instrument to retain the proximal end of the bone canal preparation instrument within the bore.

The elongate neck part may comprise;
a proximal part and a distal part;
wherein the proximal part comprises a head attachment portion and an actuator bore;
wherein the distal part comprises the pair of arms, wherein the arms extend from the body portion, and wherein the bore for receiving the proximal end of the bone canal preparation instrument passes through the pair of arms,
wherein the proximal part of the elongate neck part is detachable from the distal part. The method may further comprise attaching the proximal part to the distal part to pinch together the pair of arms to cause an inner wall of the bore to urge against the bone canal preparation instrument to retain the proximal end of the bone canal preparation instrument within the bore.

The pair of arms may be threaded at a proximal end of the distal part for connection to a corresponding thread on an inner wall of the actuator bore of the proximal part.

The proximal end of the distal part may comprise at least one protrusion on an outer surface of the pair of arms. At least one protrusion may extend from an inner wall of the actuator bore. The method may further comprise attaching the proximal part to the distal part to position a distal surface of the at least one protrusion on the proximal end of the distal part in abutment with a proximal surface of the at least one protrusion on the proximal part to cause the pair of arms to pinch together to cause an inner wall of the bore to urge against the bone canal preparation instrument to retain the proximal end of the bone canal preparation instrument within the bore.

The pair of arms may comprise an anteriorly located arm and a posteriorly located arm.

BRIEF DESCRIPTION OF THE DRAWINGS

Embodiments of this disclosure will be described hereinafter, by way of example only, with reference to the accompanying drawings in which like reference signs relate to like elements and in which.

DETAILED DESCRIPTION

Embodiments of this disclosure are described in the following with reference to the accompanying drawings.

Referring to FIGS. 1 to 8 there is shown a trial neck. The trial neck 2 has a body portion 4. The body portion 4 includes a bore 6. The bore 6 may be a blind bore (closed at its proximal end), although in the embodiments shown in the Figures it is an open bore, which passes completely through the body portion 4. The bore 6 can receive the proximal end of a bone canal preparation instrument, for attaching the bone canal preparation instrument to the trial neck 2.

Figure 9:
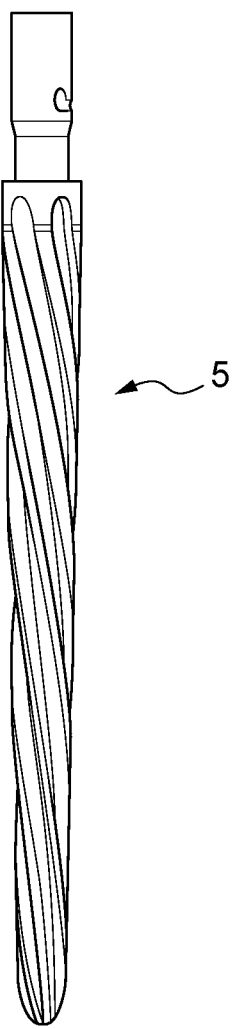
FIG. 9 shows an exemplary reamer.

The bone canal preparation instrument may, for example, be a trial stem, or a cutting instrument such as a reamer or a broach. In the following description, the bone canal preparation instrument comprises a reamer 5, but it will be appreciated that in other examples, the bone canal preparation instrument may be one of the other instruments noted above. An exemplary reamer 5 is shown in FIG. 9.

The reamer 5 itself may be in the form of an elongate shaft and may have a cutting surface located distally. The reamer 5 has a proximal end located proximally with respect to the cutting surface. The proximal end may be substantially cylindrical, with a circular cross section, although this is not essential. The proximal end may be inserted into the bore 6 of the trial neck 2 for attaching the reamer 5 to the trial neck 2, as will be described in more detail below.

As shown in FIGS. 1 to 8, the trial neck 2 also has an elongate neck part 8. The elongate neck part 8 extends from the body portion 4. The elongate neck part 8 has a proximal end 26 and a distal end 28 and a neck axis 3 which extends between the proximal 26 and distal ends 28.

A proximal end 26 of the elongate neck part 8 may be configured to be attached to a trial head 30. In other examples, the trial head 30 may be integral with the trial neck 2 (not shown).

The elongate neck part 8 includes a pair of arms 10 extending from the body portion 4. The pair of arms extend from the elongate neck part 8 and around the bore 6 to join with the body portion 4 such that the bore 6 for receiving the proximal end of the reamer 5 may pass through the pair of arms 10.

The bore 6 is defined by a bore annulus. The bore annulus is broken, such that there is a gap 66 in the wall of the bore which may extend the length of the bore 6. The pair of arms are positioned such that one arm is located on either side of a break in the bore annulus. The break in the bore annulus promotes distortion of the bore 6 when the pair of arms 10 are pinched together.

The trial neck 2 comprises a clamping mechanism 12 for attaching the proximal end of the reamer 5 to the trial neck 2. The clamping mechanism 12 is a live spring formed by the body portion 4 and the pair of arms 10 of the elongate neck part 8. The clamping mechanism 12 can be used to lock the proximal end of the reamer 5 within the bore 6, so as to prevent movement of the reamer 5 with respect to the trial neck 2 and/or inadvertent decoupling of the trial neck 2 from the reamer 5.

The trial neck 2 also comprises an actuator 24 for moving the clamping mechanism 12 between a clamping configuration and a non-clamping configuration. In the clamping configuration, the pair of arms 10 of the elongate neck part 8 are pinched together to cause an inner wall 16 of the bore 6 to urge against the reamer 5 to retain the proximal end of the reamer 5 within the bore 6.

Specific features of the different embodiments of this disclosure will now be discussed separately and in more detail, in which like features are indicated with like reference numerals.

Figure 1:
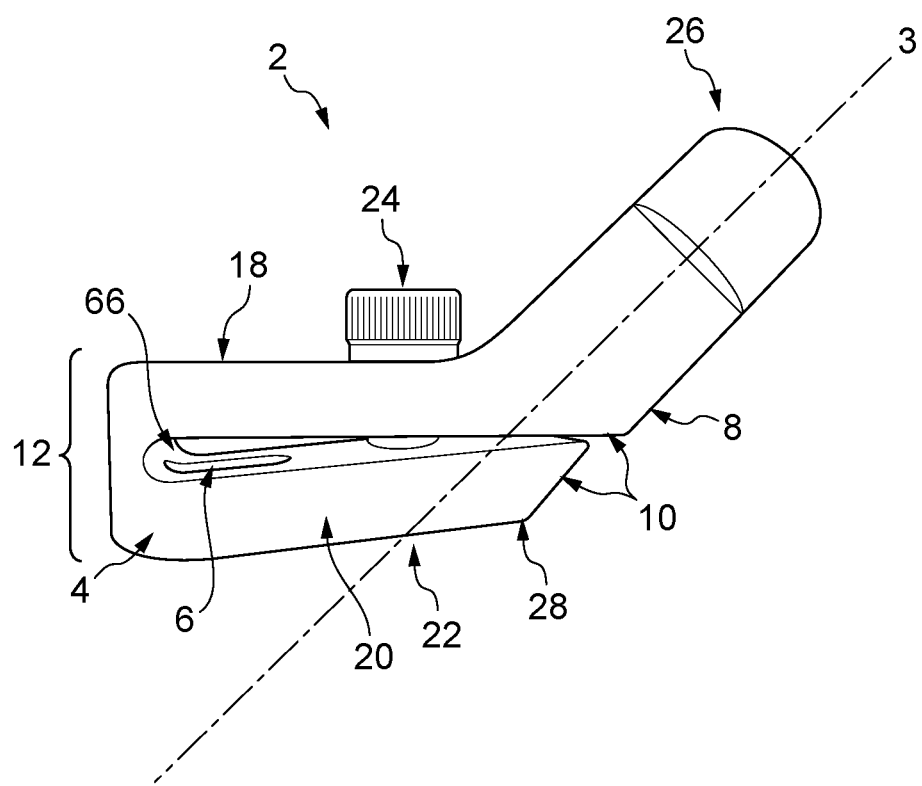
FIG. 1 shows an anterior view of a trial neck, according to an embodiment of this disclosure.
Figure 2:
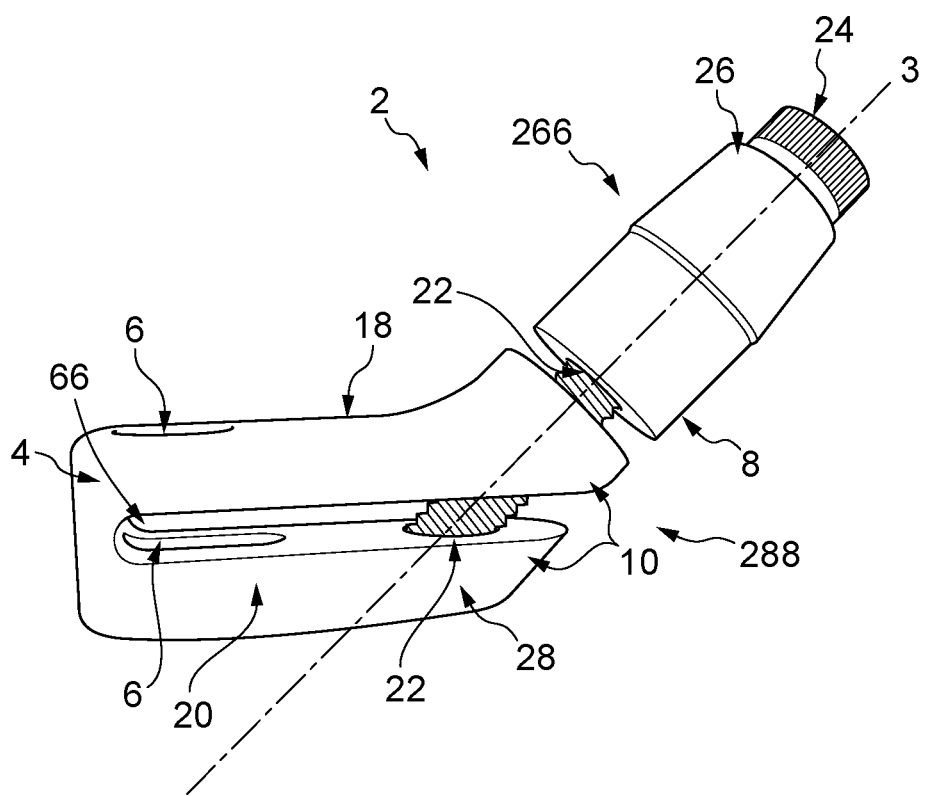
FIG. 2 shows an anterior view of a trial neck, according to another embodiment of this disclosure.
Figure 3:
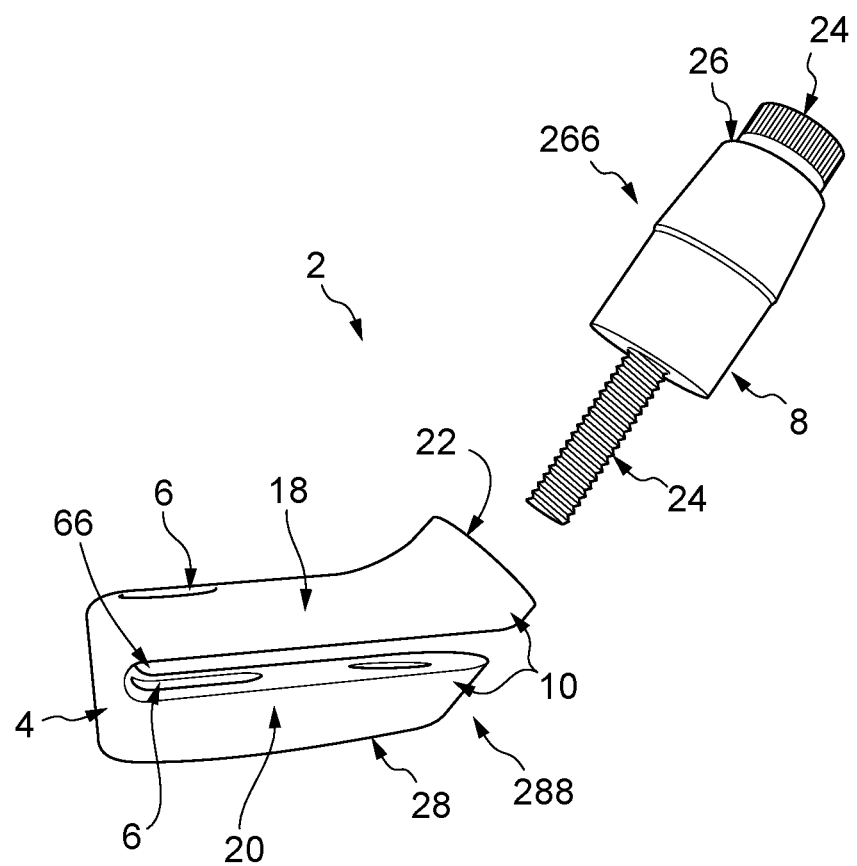
FIG. 3 shows an anterior view of the trial neck of FIG. 2 with the proximal part detached from the distal part.

In the embodiment shown in FIGS. 1 to 3, the pair of arms 10 includes a superior arm 18 and an inferior arm 20. The pair of arms 10 are positioned such that one arm is located on either side of the gap 66 in the bore annulus. As shown in FIGS. 1 to 3, the gap 66 can be transverse to the bore axis.

As may be appreciated from FIGS. 1 to 3, the actuator 24 can be a threaded actuation member which causes the clamping mechanism 12 to move into the clamping configuration as the actuator 24 is threaded through the actuator bore 22. The actuator bore 22 may extend through the pair of arms 10. The actuator bore 22 may include a corresponding thread for cooperation with the thread of the actuator 24. The actuator bore 22 may be partially threaded and may be arranged such that the inferior arm 20 may include a threaded portion of the actuator bore 22, while the superior arm 18 may include an unthreaded portion of the actuator bore 22. Alternatively, the superior arm 18 may include a threaded portion of the actuator bore 22, while the inferior arm 20 may include an unthreaded portion of the actuator bore 22. A proximal end of the actuator 24 may comprise a connection feature for connecting a corresponding connection feature of a tool to the actuator 24 for actuating the actuator 24.

As shown in FIGS. 1 to 3, the actuator 24 may be a screw.

The actuator bore 22 may extend substantially parallel to the bore 6 for receiving the proximal end of the reamer 5, as shown in FIG. 1. Alternatively, the actuator bore 22 may extend from the proximal end 26 to the distal end 28 of the elongate neck part 8 such that the actuator bore 22 extends substantially parallel to a neck axis 3. This is shown for example in FIGS. 2 and 3. In this embodiment, the proximal part 266 of the elongate neck part 8 may be detachable from the distal part 288. Alternatively, the elongate neck part 8 may be a single piece with the actuator bore 22 extending substantially parallel to the neck axis 3 in the same way.

In FIG. 2, the proximal part 266 is shown in connection with the distal part 288 via the actuator 24. Rotation of the actuator 24 within the actuator bore 22 (for example using a tool) can cause the actuator to move back and forth within the actuator bore 22. As the actuator 24 is threaded through the partially threaded actuator bore 22, it pulls the inferior arm 16 towards the superior arm 18 which causes the clamping mechanism 12 to move from a non-clamping configuration to a clamping configuration. As previously described, this movement causes the pair of arms 10 of the elongate neck part 8 to pinch together, causing the inner wall 16 of the bore 6 to urge against the reamer 5 thus retaining the proximal end of the reamer 5 within the bore 6. FIG. 3 shows the proximal part 266 and the actuator 24 detached from the distal part 288 of the elongate neck part 8.

Figure 4:
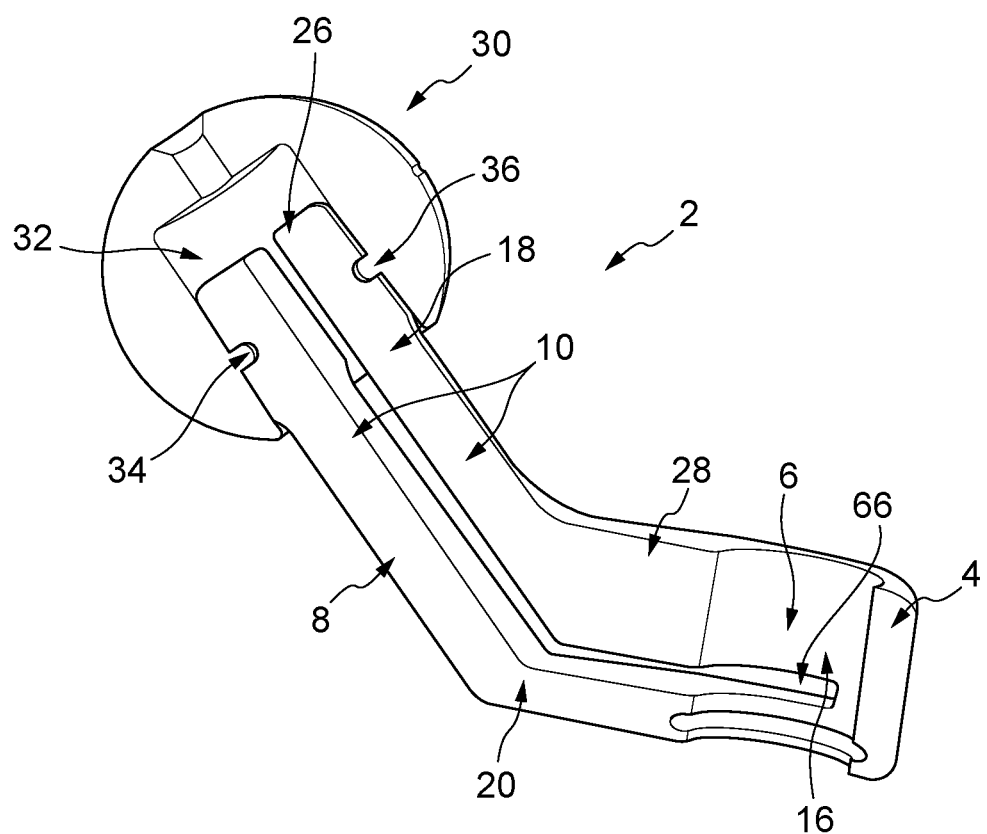
FIG. 4 shows a cross section of a trial neck, according to a further embodiment of this disclosure.
Figure 5:
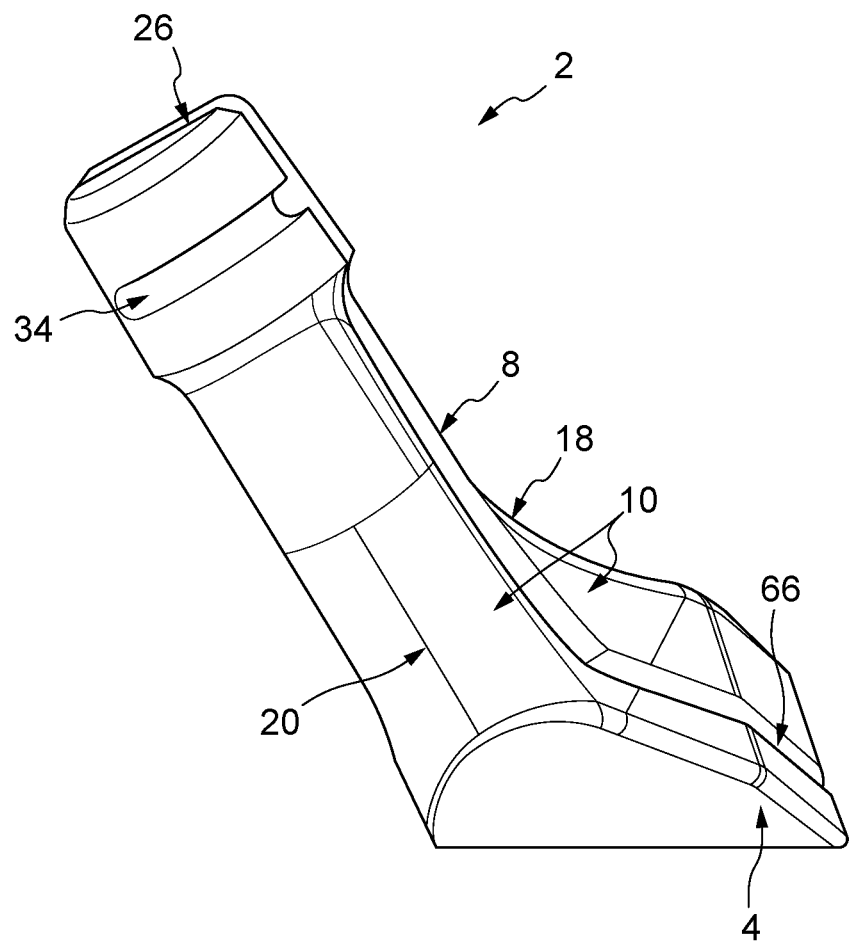
FIG. 5 shows an inferior view of the trial neck of FIG. 4.
Figure 6:
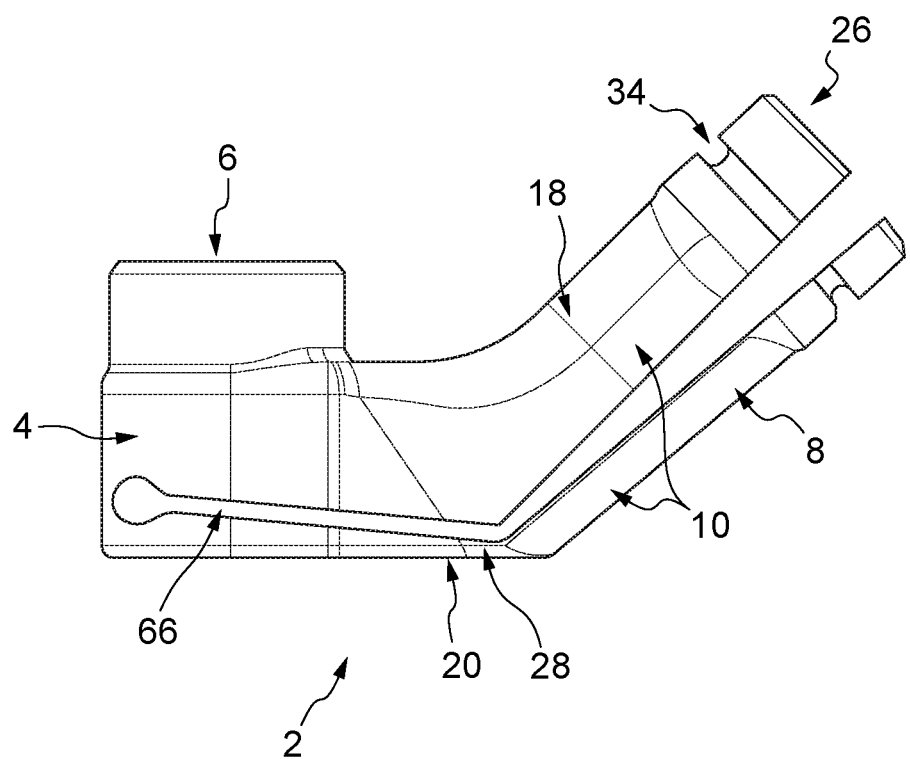
FIG. 6 shows an anterior view of the trial neck of FIG. 4 with the trial head removed.

In the embodiments shown in FIGS. 4 to 6, the actuator 24 is a trial head 30. The proximal end 26 of the elongate neck part 8 may include connection feature(s) for connection to complementary features on the trial head 30. The embodiments shown in FIGS. 4 to 6 include a superior arm 18 and an inferior arm 20. The pair of arms 10 are positioned such that one arm is located on either side of the gap 66 in the bore annulus. The gap 66 is transverse to the bore axis.

The trial head 30 of FIG. 4 includes a trial head bore 32 which may have a projection 36 located on the inner wall of the bore 32. A corresponding recess 34 may be located on the proximal part 266 of the elongate neck part 8. In this embodiment, the proximal end 26 of the elongate neck part 8 may be formed from a superior arm 18 and an inferior arm 20. As such each of the superior arm 18 and the inferior arm 20 may have a projection 36 for connection with a corresponding recess 34 in the inner bore 32 of the trial head 30. Alternatively, the recess 34 could be located on the inner wall of the trial head bore 32, and the projection 36 could be located on the proximal part 266 of the elongate neck part 8. There may be a single projection 36 or two or more projections 36.

FIG. 5 shows the recess 34 of the inferior arm 20 in more detail.

The effect of the clamping mechanism 12 can be seen by comparing FIGS. 4 and 6. FIG. 6 shows the trial neck 2 in the non-clamping configuration, without the trial head 30 attached. FIG. 4 shows the trial neck 2 in the clamping configuration, with the trial head 30 attached. As the trial head 30 is connected to the proximal end 26 of the elongate neck part 8, it pinches the inferior arm 16 and superior arm 18 together, decreasing the space between the arms. This causes the clamping mechanism 12 to move from a non-clamping configuration to a clamping configuration because as the arms are pinched together, the movement causes the inner wall 16 of the bore 6 to deform, reducing the size of the bore 6.

In one embodiment, the trial head 30 may be attached to the trial neck 2 by pinching together the superior and inferior arms and inserting the proximal end 26 of the elongate neck part 8 into the trial head bore 32 until the projection(s) 36 mates with the recess 34 to hold the trial head 30 in place.

In another embodiment, the recess 34 may have a variable depth along its length such that rotation of the projection(s) 36 within the recess 34 causes the pair of arms 10 of the elongate neck part 8 to be pinched together to a greater or lesser amount relative to the depth of the recess 34. The projection(s) 36 can be rotated within the recess 34 by rotating the trial head 30 once the projection(s) have mated with the recess 34.

Figure 7:
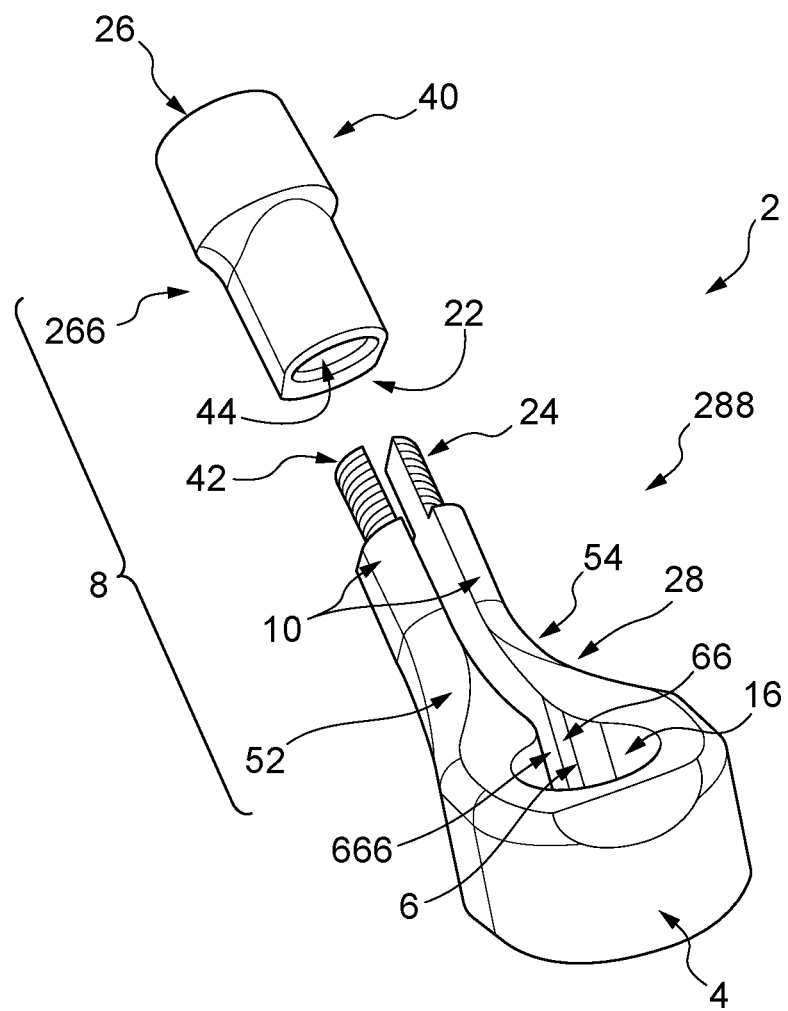
FIG. 7 shows a trial neck according to another embodiment of the disclosure.

FIG. 7 shows a different embodiment having an anterior arm 52 and a posterior arm 54. As with previously described embodiments, the distal end 28 of the pair of arms 10 extend around the bore 6 to join with the body portion 4 such that the bore 6 for receiving the proximal end of the reamer 5 passes through the pair of arms 10. The pair of arms 10 are positioned such that one arm is located on either side of the gap 666 in the bore annulus. In this embodiment, the gap 666 is a longitudinal gap 666, extending the length of the bore (parallel to the bore axis).

A head attachment portion 40, for attachment to a trial head (not shown) forms the proximal part 266 of the elongate neck part 8. The connection of the proximal part 266 with the distal part 288 causes the clamping mechanism 12 to move from a non-clamping configuration to a clamping configuration. As previously described, this movement causes the inner wall 16 of the bore 6 to urge against the reamer 5 thus retaining the proximal end of the reamer 5 within the bore 6.

As shown in FIG. 7, the proximal end 42 of the distal part 288 comprises a threaded actuator 24 in the form of a head attachment portion 40 of the elongate neck part 8. The threaded actuator 24 includes threads on the outer surface of the anterior and posterior arms 52, 54. The head attachment portion 40 comprises an actuator bore 22 at its distal end. The actuator bore may contain a corresponding thread on its inner wall 44, for mating with the threaded actuator 24 on the pair of arms 10. The proximal end 42 of the distal part 288 can be inserted into the actuator bore of the proximal part 266, and rotation of the head attachment portion 40 causes the clamping mechanism 12 to move from a non-clamping configuration to a clamping configuration due to the engagement of the threaded components.

Figure 8:
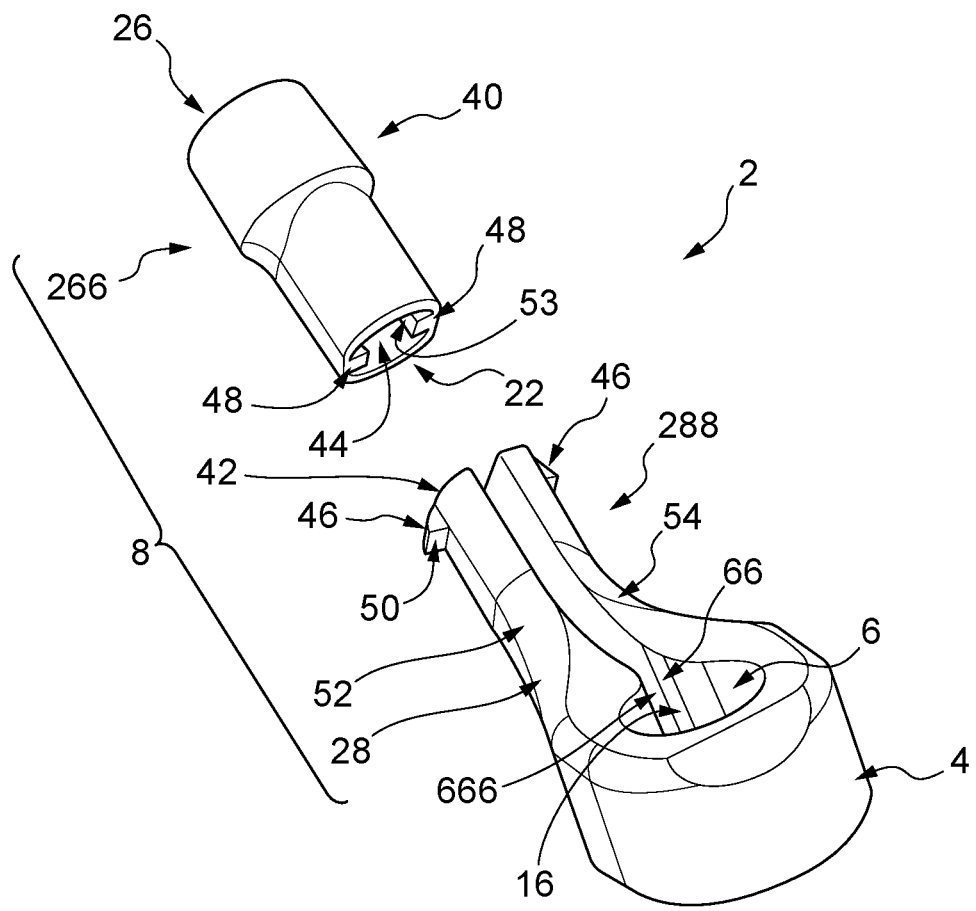
FIG. 8 shows a trial neck according to another embodiment of the disclosure.

An alternative embodiment is shown in FIG. 8, this embodiment also includes an anterior arm 52 and a posterior arm 54. As with previously described embodiments, the distal end 28 of the pair of arms 10 extend around the bore 6 to join with the body portion 4 such that the bore 6 for receiving the proximal end of the reamer 5 may pass through the pair of arms 10. The pair of arms 10 and the body portion 4 form the distal part 288 of the trial neck 2. A head attachment portion 40, for attachment to a trial head (not shown) forms the proximal part 266 of the elongate neck part 8.

In the embodiment of FIG. 8, the pair of arms 10 are positioned such that one arm is located on either side of the gap 666, which extends the length of the bore (parallel to the bore axis).

As shown in FIG. 8, the proximal end 42 of the distal part 288 comprises at least one protrusion 46 on an outer surface of the pair of arms 10. The head attachment portion 40 comprises an actuator bore 22 at its distal end. At least one protrusion 48 may also extend from an inner wall 44 of the actuator bore 22. When assembled, a distal surface 50 of the at least one protrusion 46 on the proximal end 42 of the distal part 288 abuts a proximal surface 53 of the at least one protrusion 48 on the proximal part 266. As such, attachment of the proximal part 266 to the distal part 288 causes the pair of arms 10 to pinch together to move the clamping mechanism 12 from a non-clamping configuration to a clamping configuration. As previously described, this movement causes the inner wall 16 of the bore 6 to urge against the reamer 5 thus retaining the proximal end of the reamer 5 within the bore 6.

Figure 10:
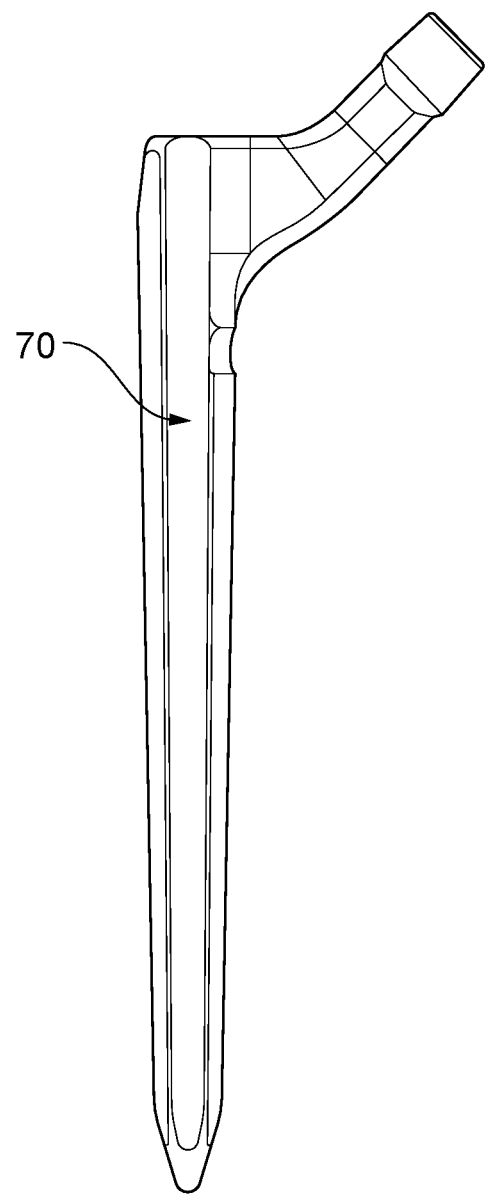
FIG. 10 shows an exemplary femoral stem prosthetic.

According to an embodiment of this disclosure, there may be provided a surgical kit comprising a trial neck (for example a trial neck 2 of the kind described above) and a reamer 5. The surgical kit may further comprise a trial head 30 having a bore 32 for receiving the proximal end 266 of the elongate neck part 8 to releasably attach the trial head 30 to the trial neck 2. It is envisaged that the kit may include further components (e.g. one or more differently sized trial necks of the kind described above, one or more different kinds of reamer 5, one or more trial heads, and/or any other components). An exemplary reamer 5 is shown in FIGS. 9 and 10. Note that the geometry of the proximal end of the reamer 5 illustrates one of many examples which may be used with the neck trial 2 of the present disclosure.

FIG. 10 shows an exemplary femoral stem 70 prosthetic component which may be inserted following preparation of the femur using any embodiments listed above.

Figure 11:
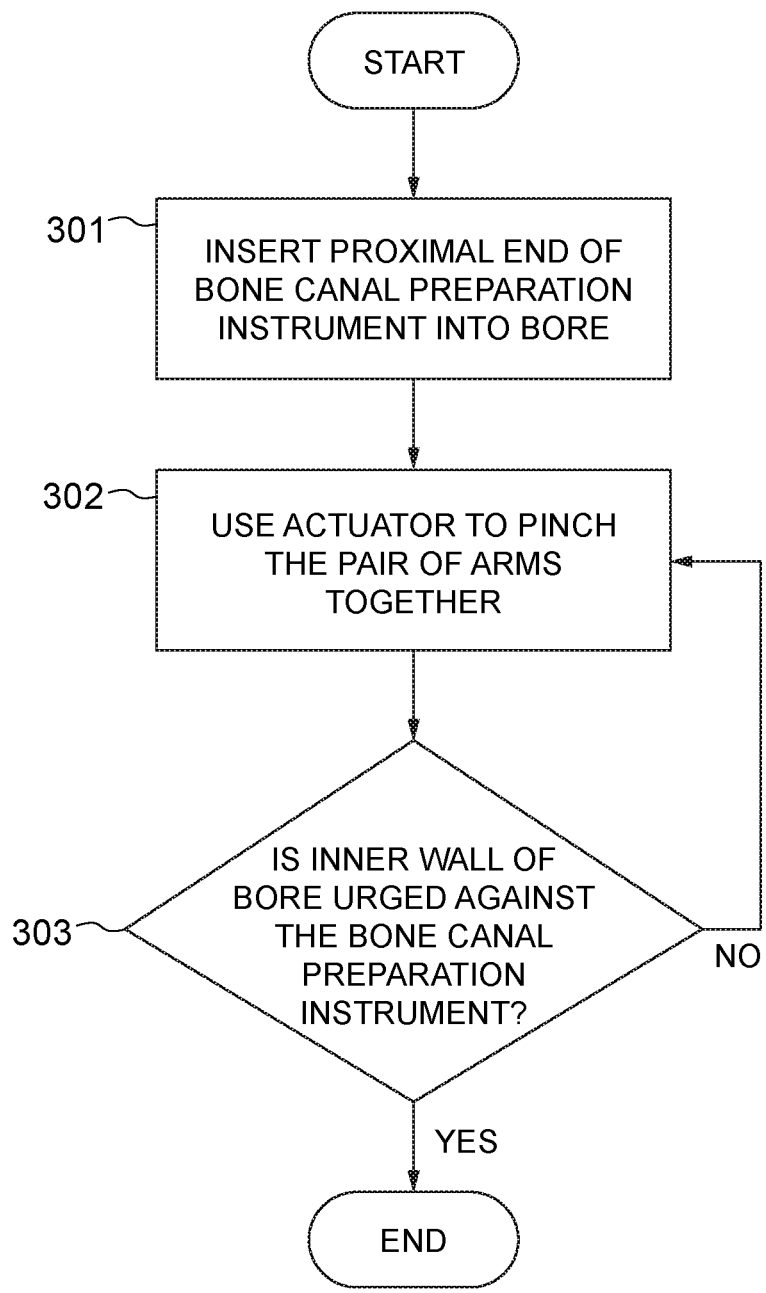
FIG. 11 is a flow chart showing the method according to another embodiment of the disclosure.

According to a further embodiment of this disclosure, there may be provided a method of attaching a trial neck (for example a trial neck 2 of the kind described above) to a reamer 5, as shown in the flow chart of FIG. 11.

Figure 12:
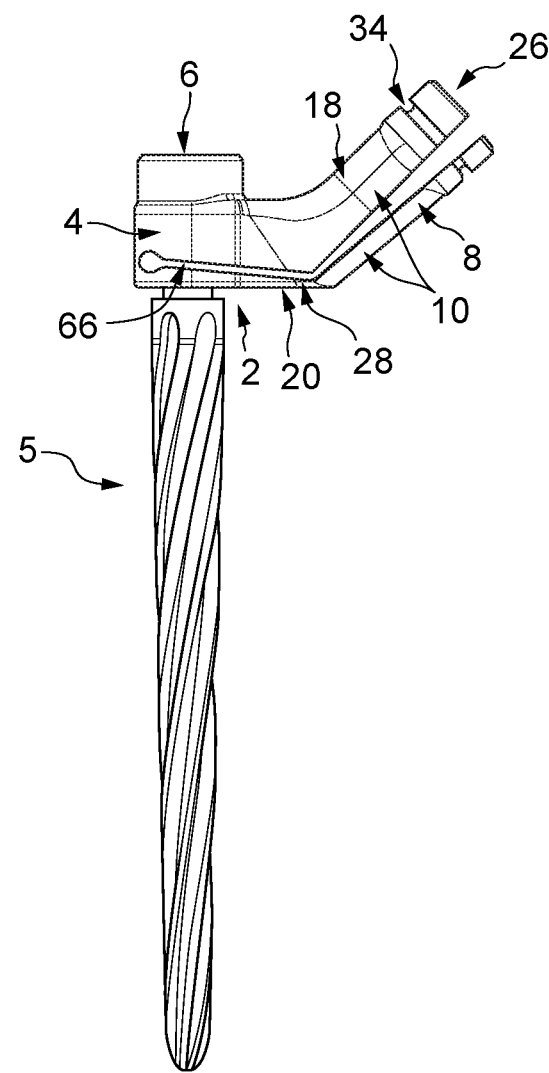
FIG. 12 shows an exemplary reamer attached to the trial neck of FIG. 6.

The method may include a step 301 of inserting the proximal end of a reamer 5 into the bore 6 of the trial neck 2, as shown in FIG. 12.

The method may also include connecting a tool to a connection feature on the actuator 24 for actuating the actuator 24. For example, a tool such as a screwdriver may be used when the actuator 24 is a screw.

The method may include a step 302 of using the actuator 24 to pinch the pair of arms 10 of the elongate neck part 8 together to cause an inner wall 16 of the bore 6 to urge against the reamer 5.

In a subsequent step 303, the user can check whether the inner wall 16 of the bore 6 is urged against the reamer 5. It may be necessary to repeat step 302 until the actuator has sufficiently pinched together the pair of arms 10 enough to urge the inner wall 16 of the bore 6 against the reamer 5 so that the reamer 5 is attached to the trial neck 2.

The actuator may comprise a trial head 30. As such, step 302 of the method may include placing a trial head 30 over the proximal end 266 of the elongate neck part 8 to pinch together the pair of arms 10 of the elongate neck part 8. The method may include rotating the trial head 30 to rotate a projection 36 within a recess 34 to cause the pair of arms 10 of the elongate neck part 8 to pinch together.

The actuator may comprise a proximal part 266. As such, step 302 of the method may include attaching a proximal part 266 to a distal part 288 to position a distal surface 50 of at least one protrusion 46 on the proximal end 42 of the distal part 288 in abutment with a proximal surface 53 of at least one protrusion 48 on the proximal part 266 to cause the pair of arms 10 to pinch together.

Accordingly, there has been described a trial neck for hip surgery and a method of attaching a trial neck to a bone canal preparation instrument. The trial neck includes a body portion having a bore for receiving a proximal end of the bone canal preparation instrument. The trial neck also includes an elongate neck part comprising a pair of arms extending from the body portion. The trial neck further includes a clamping mechanism comprising a live spring formed by the body portion and said pair of arms of the elongate neck part and an actuator, for moving the clamping mechanism between a clamping configuration and a non-clamping configuration. In the clamping configuration, the pair of arms of the elongate neck part are pinched together to cause an inner wall of the bore to urge against the bone canal preparation instrument to retain the proximal end of the bone canal preparation instrument within the bore.

Aspects of the present disclosure are set out in the following series of numbered clauses.

1. A trial neck for releasable attachment to a bone canal preparation instrument, the trial neck comprising:
    a body portion having a bore for receiving a proximal end of the bone canal preparation instrument;
    an elongate neck part comprising a pair of arms extending from the body portion;
    a clamping mechanism comprising a live spring formed by the body portion and said pair of arms of the elongate neck part; and
    an actuator, for moving the clamping mechanism between a clamping configuration and a non-clamping configuration, wherein in the clamping configuration, the pair of arms of the elongate neck part are pinched together to cause an inner wall of the bore to urge against the bone canal preparation instrument to retain the proximal end of the bone canal preparation instrument within the bore.
2. The trial neck of clause 1, wherein the pair of arms extend from the elongate neck part into the body portion, and wherein the bore for receiving the proximal end of the bone canal preparation instrument passes through the pair of arms.
3. The trial neck of clauses 1 or 2, wherein the bore is defined by a bore annulus and wherein the pair of arms are positioned such that an arm is located on either side of a break in the bore annulus.
4. The trial neck of any of clauses 1 to 3, wherein the pair of arms comprises a superiorly located arm and an inferiorly located arm.
5. The trial neck of clause 4, wherein:
    a partially threaded actuator bore extends through the pair of arms;
    wherein the actuator comprises a threaded actuation member extending within the partially threaded actuator bore; and
    wherein one of the superior or inferior arm comprises an unthreaded portion of the actuator bore, and the other of the superior or inferior arm comprises a threaded portion of the actuator bore.
6. The trial neck of clause 5, wherein the actuator bore extends substantially parallel to the bore for receiving the proximal end of the bone canal preparation instrument.
7. The trial neck of clause 5, wherein the elongate neck part comprises
    a proximal end;
    a distal end; and
    a neck axis extending between the proximal and distal ends,
    wherein the actuator bore extends from the proximal end to the distal end of the elongate neck part such that the actuator bore extends substantially parallel to a neck axis.
8. The trial neck of clause 5, wherein the elongate neck part comprises;
    a proximal part, a distal part, and a neck axis extending between the proximal and distal parts;
    wherein the distal part comprises the pair of arms;
    wherein the threaded actuator bore and threaded actuation member are substantially parallel to the neck axis; and
    wherein the proximal part is detachable from the distal part, wherein attachment of the proximal part onto the distal part causes the pair of arms of the elongate neck part to be pinched together to cause an inner wall of the bore to urge against the bone canal preparation instrument to retain the proximal end of the bone canal preparation instrument within the bore.
9. The trial neck of clause 1, wherein the actuator comprises a trial head having a bore for connection to the trial neck, wherein attachment of the trial head over the proximal end of the elongate neck part causes the pair of arms of the elongate neck part to be pinched together to cause an inner wall of the bore to urge against the bone canal preparation instrument to retain the proximal end of the bone canal preparation instrument within the bore.
10. The trial neck of clause 9, wherein the pair of arms include a recess for engagement with a corresponding projection inside the bore of the trial head, wherein the recess has a variable depth along its length, and wherein rotation of the projection within the recess causes the pair of arms of the elongate neck part to be pinched together to cause an inner wall of the bore to urge against the bone canal preparation instrument to retain the proximal end of the bone canal preparation instrument within the bore.
11. The trial neck of clause 1, wherein the elongate neck part comprises;
    a proximal part and a distal part;
    wherein the proximal part comprises a head attachment portion and an actuator bore;
    wherein the distal part comprises the pair of arms, wherein the arms extend from the body portion, and wherein the bore for receiving the proximal end of the bone canal preparation instrument passes through the pair of arms,
    wherein the proximal part of the elongate neck part is detachable from the distal part, and wherein attachment of the proximal part to the distal part causes the pair of arms to pinch together to cause an inner wall of the bore to urge against the bone canal preparation instrument to retain the proximal end of the bone canal preparation instrument within the bore.

12. The neck trial of clause 11, wherein the pair of arms is threaded at a proximal end of the distal part for connection to a corresponding thread on an inner wall of the actuator bore of the proximal part.

13. The trial neck of clause 11, wherein a proximal end of the distal part comprises at least one protrusion on an outer surface of the pair of arms,
wherein at least one protrusion extends from an inner wall of the actuator bore;
wherein when assembled, a distal surface of the at least one protrusion on the proximal end of the distal part abuts a proximal surface of the at least one protrusion on the proximal part and wherein attachment of the proximal part to the distal part causes the pair of arms to pinch together to cause an inner wall of the bore to urge against the bone canal preparation instrument to retain the proximal end of the bone canal preparation instrument within the bore.

14. The trial neck of any of clauses 11 to 13, wherein the pair of arms comprises an anteriorly located arm and a posteriorly located arm.

15. A surgical kit comprising:
a trial neck according to any preceding claim; and
a bone canal preparation instrument.

16. The surgical kit of clause 15, further comprising a trial head having a bore for receiving the proximal end of the elongate neck part to releasably attach the trial head to the trial neck.

17. The surgical kit of clauses 15 or 16, further comprising a prosthetic stem component.

18. A method of attaching a trial neck to a bone canal preparation instrument, the trial neck comprising:
a body portion having a bore for receiving a proximal end of the bone canal preparation instrument;
an elongate neck part comprising a pair of arms extending from the body portion;
a clamping mechanism comprising a live spring formed by the body portion and said pair of arms of the elongate neck part; and
an actuator, for moving the clamping mechanism between a clamping configuration and a non-clamping configuration, the method comprising:
inserting the proximal end of the bone canal preparation instrument into the bore; and
using the actuator to pinch the pair of arms of the elongate neck part together to cause an inner wall of the bore to urge against the bone canal preparation instrument.

19. The method of clause 18, wherein the pair of arms extend from the elongate neck part into the body portion, and wherein the bore for receiving the proximal end of the bone canal preparation instrument passes through the pair of arms.

20. The method of clauses 18 or 19, wherein the bore is defined by a bore annulus and wherein the pair of arms are positioned such that an arm is located on either side of a break in the bore annulus.

21. The method of any of clauses 18 to 20, wherein the pair of arms comprises a superiorly located arm and an inferiorly located arm.

22. The method of any of clauses 18 to 21, wherein a partially threaded actuator bore extends through the pair of arms and wherein the actuator comprises a threaded actuation member extending within the partially threaded actuator bore.

23. The method of clause 22, wherein the actuator bore extends substantially parallel to the bore for receiving the proximal end of the bone canal preparation instrument.

24. The method of clause 22, wherein the elongate neck part comprises
a proximal end;
a distal end; and
a neck axis extending between the proximal and distal ends,
wherein the actuator bore extends from the proximal end to the distal end of the elongate neck part such that the actuator bore extends substantially parallel to a neck axis.

25. The method of clause 22, wherein the elongate neck part comprises;
a proximal part, a distal part, and a neck axis extending between the proximal and distal parts;
wherein the distal part comprises the pair of arms;
wherein the threaded actuator bore and threaded actuation member are substantially parallel to the neck axis; and
wherein the proximal part is detachable from the distal part, wherein attachment of the proximal part onto the distal part causes the pair of arms of the elongate neck part to be pinched together to cause an inner wall of the bore to urge against the bone canal preparation instrument to retain the proximal end of the bone canal preparation instrument within the bore.

26. The method of clause 18, wherein the actuator comprises a trial head having a bore for connection to the trial neck, wherein the method further comprises placing the trial head over the proximal end of the elongate neck part to pinch together the pair of arms of the elongate neck part, causing an inner wall of the bore to urge against the bone canal preparation instrument to retain the proximal end of the bone canal preparation instrument within the bore.

27. The method of clause 26, wherein the pair of arms include a recess for engagement with a corresponding projection inside the bore of the trial head, wherein the recess has a variable depth along its length, and wherein the method further comprises rotating trial head to rotate the projection within the recess to cause the pair of arms of the elongate neck part to pinch together to cause an inner wall of the bore to urge against the bone canal preparation instrument to retain the proximal end of the bone canal preparation instrument within the bore.

28. The method of clause 18, wherein the elongate neck part comprises;
a proximal part and a distal part;
wherein the proximal part comprises a head attachment portion and an actuator bore;
wherein the distal part comprises the pair of arms, wherein the arms extend from the body portion, and wherein the bore for receiving the proximal end of the bone canal preparation instrument passes through the pair of arms,
wherein the proximal part of the elongate neck part is detachable from the distal part, and wherein the method further comprises attaching the proximal part to the distal part to pinch together the pair of arms to cause an inner wall of the bore to urge against the bone canal preparation instrument to retain the proximal end of the bone canal preparation instrument within the bore.
29. The method of clause 28, wherein the pair of arms is threaded at a proximal end of the distal part for connection to a corresponding thread on an inner wall of the actuator bore of the proximal part.
30. The method of clause 28, wherein a proximal end of the distal part comprises at least one protrusion on an outer surface of the pair of arms,
wherein at least one protrusion extends from an inner wall of the actuator bore;
wherein the method further comprises attaching the proximal part to the distal part to position a distal surface of the at least one protrusion on the proximal end of the distal part in abutment with a proximal surface of the at least one protrusion on the proximal part to cause the pair of arms to pinch together to cause an inner wall of the bore to urge against the bone canal preparation instrument to retain the proximal end of the bone canal preparation instrument within the bore.
31. The method of any of clauses 28 to 30, wherein the pair of arms comprises an anteriorly located arm and a posteriorly located arm.

Although particular embodiments of this disclosure have been described, it will be appreciated that many modifications/additions and/or substitutions may be made within the scope of the claims.

What is claimed is:

1. A trial neck for releasable attachment to a bone canal preparation instrument, the trial neck comprising:
   a body portion having a bore for receiving a proximal end of the bone canal preparation instrument;
   an elongate neck part comprising a pair of arms extending from the body portion, wherein a partially threaded actuator bore extends through the pair of arms;
   a clamping mechanism comprising a live spring formed by the body portion and said pair of arms of the elongate neck part; and
   an actuator, for moving the clamping mechanism between a clamping configuration and a non-clamping configuration, wherein the actuator comprises a threaded actuation member extending within the partially threaded actuator bore, and
   wherein in the clamping configuration, the pair of arms of the elongate neck part are pinched together to cause an inner wall of the bore to urge against the bone canal preparation instrument to retain the proximal end of the bone canal preparation instrument within the bore.

2. The trial neck of claim 1, wherein the pair of arms extend from the elongate neck part into the body portion, and wherein the bore for receiving the proximal end of the bone canal preparation instrument passes through the pair of arms.

3. The trial neck of claim 2, wherein the bore is defined by a bore annulus and wherein the pair of arms are positioned such that an arm is located on either side of a break in the bore annulus.

4. The trial neck of claim 1, wherein the pair of arms comprises a superiorly located arm and an inferiorly located arm.

5. The trial neck of claim 4, wherein:
   wherein one of the superior or inferior arm comprises an unthreaded portion of the actuator bore, and the other of the superior or inferior arm comprises a threaded portion of the actuator bore.

6. The trial neck of claim 5, wherein the actuator bore extends substantially parallel to the bore for receiving the proximal end of the bone canal preparation instrument.

7. The trial neck of claim 5, wherein the elongate neck part comprises
   a proximal end;
   a distal end; and
   a neck axis extending between the proximal and distal ends,
   wherein the actuator bore extends from the proximal end to the distal end of the elongate neck part such that the actuator bore extends substantially parallel to a neck axis.

8. The trial neck of claim 5, wherein the elongate neck part comprises;
   a proximal part, a distal part, and a neck axis extending between the proximal and distal parts;
   wherein the distal part comprises the pair of arms;
   wherein the threaded actuator bore and threaded actuation member are substantially parallel to the neck axis; and
   wherein the proximal part is detachable from the distal part, wherein attachment of the proximal part onto the distal part causes the pair of arms of the elongate neck part to be pinched together to cause an inner wall of the bore to urge against the bone canal preparation instrument to retain the proximal end of the bone canal preparation instrument within the bore.

9. The trial neck of claim 1, wherein the actuator comprises a trial head having a bore for connection to the trial neck, wherein attachment of the trial head over the proximal end of the elongate neck part causes the pair of arms of the elongate neck part to be pinched together to cause an inner wall of the bore to urge against the bone canal preparation instrument to retain the proximal end of the bone canal preparation instrument within the bore.

10. The trial neck of claim 9, wherein the pair of arms include a recess for engagement with a corresponding projection inside the bore of the trial head, wherein the recess has a variable depth along its length, and wherein rotation of the projection within the recess causes the pair of arms of the elongate neck part to be pinched together to cause an inner wall of the bore to urge against the bone canal preparation instrument to retain the proximal end of the bone canal preparation instrument within the bore.

11. The trial neck of claim 1, wherein the elongate neck part comprises;
   a proximal part and a distal part;
   wherein the proximal part comprises a head attachment portion and an actuator bore;
   wherein the distal part comprises the pair of arms, wherein the arms extend from the body portion, and wherein the bore for receiving the proximal end of the bone canal preparation instrument passes through the pair of arms,
   wherein the proximal part of the elongate neck part is detachable from the distal part, and wherein attachment of the proximal part to the distal part causes the pair of arms to pinch together to cause an inner wall of the bore to urge against the bone canal preparation instrument to retain the proximal end of the bone canal preparation instrument within the bore.

12. The trial neck of claim 11, wherein the pair of arms is threaded at a proximal end of the distal part for connection to a corresponding thread on an inner wall of the actuator bore of the proximal part.

13. The trial neck of claim 11, wherein a proximal end of the distal part comprises at least one protrusion on an outer surface of the pair of arms,
wherein at least one protrusion extends from an inner wall of the actuator bore;
wherein when assembled, a distal surface of the at least one protrusion on the proximal end of the distal part abuts a proximal surface of the at least one protrusion on the proximal part and wherein attachment of the proximal part to the distal part causes the pair of arms to pinch together to cause an inner wall of the bore to urge against the bone canal preparation instrument to retain the proximal end of the bone canal preparation instrument within the bore.

14. The trial neck of claim 11, wherein the pair of arms comprises an anteriorly located arm and a posteriorly located arm.

15. A surgical kit comprising:
a bone canal preparation instrument; and
a trial neck for releasable attachment to the bone canal preparation instrument, the trial neck comprising:
a body portion having a bore for receiving a proximal end of the bone canal preparation instrument;
an elongate neck part comprising a pair of arms extending from the body portion, wherein a partially threaded actuator bore extends through the pair of arms;
a clamping mechanism comprising a live spring formed by the body portion and said pair of arms of the elongate neck part; and
an actuator, for moving the clamping mechanism between a clamping configuration and a non-clamping configuration, wherein the actuator comprises a threaded actuation member extending within the partially threaded actuator bore, and
wherein in the clamping configuration, the pair of arms of the elongate neck part are pinched together to cause an inner wall of the bore to urge against the bone canal preparation instrument to retain the proximal end of the bone canal preparation instrument within the bore.

16. The surgical kit of claim 15, further comprising a trial head having a bore for receiving the proximal end of the elongate neck part to releasably attach the trial head to the trial neck.

17. The surgical kit of claim 16, further comprising a prosthetic stem component.

18. A method of attaching a trial neck to a bone canal preparation instrument, the trial neck comprising:
a body portion having a bore for receiving a proximal end of the bone canal preparation instrument;
an elongate neck part comprising a pair of arms extending from the body portion, wherein a partially threaded actuator bore extends through the pair of arms;
a clamping mechanism comprising a live spring formed by the body portion and said pair of arms of the elongate neck part; and
an actuator, for moving the clamping mechanism between a clamping configuration and a non-clamping configuration, wherein the actuator comprises a threaded actuation member extending within the partially threaded actuator bore, the method comprising:
inserting the proximal end of the bone canal preparation instrument into the bore; and
using the actuator to pinch the pair of arms of the elongate neck part together to cause an inner wall of the bore to urge against the bone canal preparation instrument.

19. The method of claim 18, wherein the pair of arms extend from the elongate neck part into the body portion, and wherein the bore for receiving the proximal end of the bone canal preparation instrument passes through the pair of arms.

20. The method of claim 19, wherein the bore is defined by a bore annulus and wherein the pair of arms are positioned such that an arm is located on either side of a break in the bore annulus.

21. The method of claim 19, wherein the pair of arms comprises a superiorly located arm and an inferiorly located arm.

22. The method of claim 19, wherein the actuator bore extends substantially parallel to the bore for receiving the proximal end of the bone canal preparation instrument.

23. The method of claim 19, wherein the elongate neck part comprises
a proximal end;
a distal end; and
a neck axis extending between the proximal and distal ends,
wherein the actuator bore extends from the proximal end to the distal end of the elongate neck part such that the actuator bore extends substantially parallel to a neck axis.

24. The method of claim 19, wherein the elongate neck part comprises;
a proximal part, a distal part, and a neck axis extending between the proximal and distal parts;
wherein the distal part comprises the pair of arms;
wherein the threaded actuator bore and threaded actuation member are substantially parallel to the neck axis; and
wherein the proximal part is detachable from the distal part, wherein attachment of the proximal part onto the distal part causes the pair of arms of the elongate neck part to be pinched together to cause an inner wall of the bore to urge against the bone canal preparation instrument to retain the proximal end of the bone canal preparation instrument within the bore.

25. The method of claim 18, wherein the actuator comprises a trial head having a bore for connection to the trial neck, wherein the method further comprises placing the trial head over the proximal end of the elongate neck part to pinch together the pair of arms of the elongate neck part, causing an inner wall of the bore to urge against the bone canal preparation instrument to retain the proximal end of the bone canal preparation instrument within the bore.

26. The method of claim 25, wherein the pair of arms include a recess for engagement with a corresponding projection inside the bore of the trial head, wherein the recess has a variable depth along its length, and wherein the method further comprises rotating trial head to rotate the projection within the recess to cause the pair of arms of the elongate neck part to pinch together to cause an inner wall of the bore to urge against the bone canal preparation instrument to retain the proximal end of the bone canal preparation instrument within the bore.

27. The method of claim 18, wherein the elongate neck part comprises;
a proximal part and a distal part;
wherein the proximal part comprises a head attachment portion and an actuator bore;
wherein the distal part comprises the pair of arms, wherein the arms extend from the body portion, and wherein the bore for receiving the proximal end of the bone canal preparation instrument passes through the pair of arms, wherein the proximal part of the elongate neck part is detachable from the distal part, and wherein the method further comprises attaching the proximal part to the distal part to pinch together the pair of arms to cause an inner wall of the bore to urge against the bone canal preparation instrument to retain the proximal end of the bone canal preparation instrument within the bore.

28. The method of claim 27, wherein the pair of arms is threaded at a proximal end of the distal part for connection to a corresponding thread on an inner wall of the actuator bore of the proximal part.

29. The method of claim 28, wherein a proximal end of the distal part comprises at least one protrusion on an outer surface of the pair of arms,
   wherein at least one protrusion extends from an inner wall of the actuator bore;
   wherein the method further comprises attaching the proximal part to the distal part to position a distal surface of the at least one protrusion on the proximal end of the distal part in abutment with a proximal surface of the at least one protrusion on the proximal part to cause the pair of arms to pinch together to cause an inner wall of the bore to urge against the bone canal preparation instrument to retain the proximal end of the bone canal preparation instrument within the bore.

30. The method of claim 27, wherein the pair of arms comprises an anteriorly located arm and a posteriorly located arm.

* * * * *